(12) United States Patent
Contractor et al.

(10) Patent No.: US 11,026,897 B2
(45) Date of Patent: Jun. 8, 2021

(54) COMPOSITION OF CURCUMAGALACTOMANNOSIDE AND HOPS EXTRACT

(71) Applicant: Metagenics, Inc., Aliso Viejo, CA (US)

(72) Inventors: Nikhat Contractor, Aliso Viejo, CA (US); Jennifer Joan Ryan, Portland, OR (US)

(73) Assignee: METAGENICS, INC., Aliso Viejo, CA (US)

( * ) Notice: Subject to any disclaimer, the term of this patent is extended or adjusted under 35 U.S.C. 154(b) by 0 days.

(21) Appl. No.: 16/536,449

(22) Filed: Aug. 9, 2019

(65) Prior Publication Data

US 2020/0046651 A1 Feb. 13, 2020

Related U.S. Application Data

(60) Provisional application No. 62/717,430, filed on Aug. 10, 2018.

(51) Int. Cl.

| | | |
|---|---|---|
| *A61K 36/906* | (2006.01) | |
| *A61K 31/12* | (2006.01) | |
| *A61K 31/085* | (2006.01) | |
| *A61K 31/366* | (2006.01) | |
| *A61P 1/04* | (2006.01) | |
| *A61K 31/519* | (2006.01) | |
| *A61K 31/714* | (2006.01) | |
| *A61K 31/198* | (2006.01) | |
| *A61K 36/53* | (2006.01) | |

(52) U.S. Cl.
CPC ............ *A61K 31/12* (2013.01); *A61K 31/085* (2013.01); *A61K 31/198* (2013.01); *A61K 31/366* (2013.01); *A61K 31/519* (2013.01); *A61K 31/714* (2013.01); *A61K 36/53* (2013.01); *A61K 36/906* (2013.01); *A61P 1/04* (2018.01)

(58) Field of Classification Search
None
See application file for complete search history.

(56) References Cited

U.S. PATENT DOCUMENTS

| | | | |
|---|---|---|---|
| 6,949,260 B2 | 9/2005 | Krumhar | |
| 7,914,831 B2 | 3/2011 | Babish et al. | |
| 8,092,846 B2 | 1/2012 | Babish et al. | |
| 8,193,201 B2 | 6/2012 | Babish et al. | |
| 8,785,380 B2* | 7/2014 | Madhavamenon | A61K 36/48 514/5.5 |
| 2004/0137096 A1 | 7/2004 | Kuhrts | |
| 2004/0219240 A1 | 11/2004 | Babish et al. | |
| 2013/0064913 A1* | 3/2013 | Tripp | A61K 36/185 424/757 |
| 2017/0020829 A1* | 1/2017 | Baron | A61K 45/06 |
| 2018/0015032 A1 | 1/2018 | LeBrun-Blashka et al. | |
| 2018/0193287 A1 | 7/2018 | Hellerbrand | |
| 2019/0224193 A1* | 7/2019 | Reid | A61K 38/1816 |
| 2020/0093851 A1* | 3/2020 | von Maltzahn | A61K 31/11 |

FOREIGN PATENT DOCUMENTS

WO 2015049561 A1 4/2015

OTHER PUBLICATIONS

Saji, Sangeeth et al. "Curcumin-galactomannoside Complex inhibits pathogenesis in Ox-LDL-challenged human peripheral blood mononuclear cells." Inflammopharmacology, vol. 26, No. 5, Apr. 9, 2018, pp. 1273-1282.

Krishnakumar, I.M. et al. "An Enhanced Bioavailable Formulation of Curcumin using Fenugreek-derived soluble dietary fibre." Journal of Functional Foods, vol. 4, No. 1, Jan. 4, 2012. pp. 348-357.

Kumar, Dinesh et al. "Enhanced Bioavailability and Relative Distribution of Free (unconjugated) curcuminoids following the Oral Administration of a Food-Grade Formulation with Fenugreek Dietary Fibre: A randomised double-blind crossover study." Journal of Functional Foods, vol. 22, No. 23, Feb. 23, 2016, pp. 578-587.

Campbell, Marilyn S. et al. "Responsiveness to Curcumin Intervention is associated with Reduced Aortic Stiffness in young, obese men with higher initial stiffness." Journal of Functional Foods, vol. 29, 2017, pp. 154-160.

International Search Report and Written Opinion of corresponding International Application No. PCT/US2019/045849, dated Nov. 5, 2019.

* cited by examiner

Primary Examiner — Ralph J Gitomer
(74) Attorney, Agent, or Firm — Warner Norcross + Judd LLP

(57) ABSTRACT

A composition for treatment of inflammation in a mammal is provided. The mammal has a neutrophil to lymphocyte ratio (NLR). The composition includes a curcumagalactomannoside and a hops extract. The curcumagalactomannoside and the hops extract cooperate to decrease the NLR of the mammal 12 weeks after ingestion of the composition. A method of treatment of inflammation in a mammal is also provided. The method includes obtaining a parameter of the mammal. The method further includes dosing the composition based on the parameter. The method further includes administering the composition to the mammal.

18 Claims, No Drawings

COMPOSITION OF CURCUMAGALACTOMANNOSIDE AND HOPS EXTRACT

CROSS-REFERENCE TO RELATED APPLICATIONS

This application claims priority to and all of advantages of U.S. Prov. Appl. No. 62/717,430, filed on 10 Aug. 2018, the contents of which is hereby incorporated by reference.

TECHNICAL FIELD

The present invention generally relates to compositions for treatment of inflammation in a mammal and, more specifically, to a composition comprising a combination of a curcumagalactomannoside and a hops extract.

BACKGROUND

Gastrointestinal inflammatory disorders are a group of chronic disorders that cause inflammation and/or ulceration in the intestinal mucous membrane. These disorders include, for example, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis. Such diseases are on the increase in western society.

Inflammatory bowel diseases (IBD) are characterized by chronic inflammation in the gastrointestinal tract and are accompanied by symptoms such as abdominal pain, fever, diarrhea, and melena. The most prevalent types of inflammatory bowel disease are ulcerative colitis (UC) and Crohn's disease (CD). Ulcerative colitis is a type of diffuse nonspecific inflammation of an unknown cause occurring in the colon, which mostly invades mucous membranes, frequently causes infection or ulcers in the GI tract, and is accompanied by symptoms including bloody diarrhea, whereas Crohn's disease is a type of granulomatous inflammation of an unknown cause that develops ulcers, fibrosis, stenosis, and lesions in the entire digestive system from mouth to anus, and is accompanied by systemic symptoms such as abdominal pain, chronic diarrhea, fever, and malnutrition. Inflammatory bowel diseases are pleiotropic in nature with contributing factors with components ranging from dysregulated immune responses (genetic) to environmental cues (intestinal microbiota). Pharmaceutical intervention (e.g., the use of drugs) for treating inflammatory bowel diseases include steroid immunosuppressive agents, 5-aminosalicylic acid (5-ASA)-based drugs that block the production of prostaglandins (e.g., sulfasalazine), mesalazine, etc. In more severe cases, corticosteroids are prescribed to treat active exacerbations and can sometimes maintain remission. Azathioprine and 6-mercaptopurine have also been used in patients who require chronic administration of corticosteroids. It has been suggested that these drugs may play a role in the long-term prophylaxis. Unfortunately, there can be a very long delay (up to six months) before onset of action in some patients. Antidiarrheal drugs can also provide symptomatic relief in some patients. Antibiotics are used in treating secondary small bowel bacterial overgrowth and in treatment of pyogenic complications.

While a number of drugs are used (and some are used off label) these may not have fully predictable therapeutic effects and may cause serious side effects, thus limiting the use of such drugs. Many of these side effects are found on the package inserts of any drug used for this purpose, and some may be life threatening. Often treatment is lifelong and relapse is common and unpredictable. To the extent such pharmaceutical treatment occurs, it may be desirable to reduce the amount of pharmaceutical treatment, and of course, to return the patient to a normal lifestyle with minimal disruption.

Relapses may be highly variable, and the onset may be insidious or abrupt, and may include diarrhea, tenesmus and relapsing rectal bleeding. With fulminant involvement of the entire colon, toxic megacolon, a life-threatening emergency, may occur. Extraintestinal manifestations include arthritis, pyoderma gangrenosum, uveitis, and erythema nodosum.

Nutritional therapy or an elemental diet can improve the nutritional status of patients and induce symptomatic improvement of acute disease. Pharmaceutical treatment does not address malnutrition, and some of their side effects include nutrient deficiencies and anemia. For example, the use of methotrexate and/or sulfasalazine has an adverse effect on folate absorption and can cause hemolytic anemia. Corticosteroids increase net protein loss. Due to the high prevalence of clinical and subclinical issues, routine monitoring of blood nutrient levels, and supplementation with minerals, vitamins and protein, are recommended.

Accordingly, it is desirable to provide an improved composition for treatment of inflammation in a mammal and methods relating to the same. Furthermore, other desirable features and characteristics will become apparent from the subsequent summary and detailed description and the appended claims, taken in conjunction with the foregoing technical field and background.

SUMMARY OF THE INVENTION

A composition for treatment of inflammation in a mammal is provided. The mammal has a neutrophil to lymphocyte ratio (NLR). The composition includes a curcumagalactomannoside and a hops extract. The curcumagalactomannoside and the hops extract cooperate to decrease the NLR of the mammal 12 weeks after ingestion of the composition.

A composition for treatment of inflammation in a mammal is also provided. The mammal has a neutrophil to lymphocyte ratio (NLR). The composition consists essentially of curcumagalactomannoside, a hops extract, a ginger root extract, a protein-containing matrix, a rosemary extract, folate, vitamin B-12, and quercetin. At least the curcumagalactomannoside and hops extract cooperate to decrease the NLR of the mammal 12 weeks after ingestion of the composition.

A method of treatment of inflammation in a mammal is also provided. The method includes obtaining a parameter of the mammal. The method further includes dosing a composition based on the parameter. The composition includes a curcumagalactomannoside and a hops extract. The method further includes administering the composition to the mammal.

DETAILED DESCRIPTION

As used herein, the singular forms "a", "an," and "the" are meant to include plural referents unless the context clearly dictates otherwise.

As used herein, an "embodiment" means that a particular feature, structure or characteristic is included in at least one or more manifestations, examples, or implementations of this invention. Furthermore, the particular features, structures or characteristics may be combined in any suitable manner, as would be apparent to a person skilled in the art. Combinations of features of different embodiments are all meant to be within the scope of the invention, without the need for explicitly describing every possible permutation by example. Thus, any of the claimed embodiments can be used in any combination.

As used herein, the term "weight percent" (and thus the associated abbreviation "wt. %") typically refers to a percent by weight expressed in terms of a weight of dry matter. As such, it is to be appreciated that a wt. % can be calculated on a basis of a total weight of a composition, or calculated from a ratio between two or more components/parts of a mixture (e.g. a total weight of dry matter).

As used herein, the terms "about" and "approximately", when referring to a specified, measurable value (such as a parameter, an amount, a temporal duration, and the like), is meant to encompass the specified value and variations of and from the specified value, such as variations of +/−10% or less, alternatively +/−5% or less, alternatively +/−1% or less, alternatively +/−0.1% or less of and from the specified value, insofar as such variations are appropriate to perform in the disclosed embodiments. Thus the value to which the modifier "about" or "approximately" refers is itself also specifically disclosed.

As used herein, the term "alleviation" refers to all kinds of activities associated with ameliorating or advantageously changing the status of inflammatory bowel disease(s) by the administration of the formulation of the present invention.

As used herein, the term "administration" refers to an activity of introducing the formulation of the present invention to a subject by an appropriate method, and the formulation may be administered via various routes of oral or parenteral routes as long as they can deliver the same to the target tissues.

As used herein, "bloodwork" and "clinical parameters" therein refers to measurements used during the study, which correlate to symptoms, quality of life, or the disease being treated. As examples, RDW refers to red cell width distribution, the RDW cutoff (the point where the results are normal vs. abnormal indicating disease) for ulcerative colitis is 14.0, and for Crohn's Disease 14.1. As another example, the term "NLR" refers to the absolute ratio of Neutrophils to Lymphocytes; the NLR cutoff for disease is 2.47. In various embodiments, a decrease in neutrophils and an increase in lymphocytes is an indication of improvement of inflammation, such as inflammation relating to inflammatory bowel disease (IBD).

As used herein, "an effective amount" refers to an amount sufficient for the treatment of diseases at a reasonable benefit/risk ratio applicable to a medical treatment, and the level of the effective dose may be determined from factors including severity of illness, drug activity, age, body weight, health conditions, drug sensitivity of a subject, administration time, administration route and dissolution rate, length of treatment of the formulation of the present invention, drug(s) used in combination with or simultaneously with the formulation of the present invention, and other factors well known in the medical field. The formulation of the present invention may be administered in an effective amount. The formulation of the present invention may be administered as an individual therapeutic agent or in combination with other therapeutic agent(s), and also sequentially or simultaneously with the conventional therapeutic agent(s). Additionally, the formulation of the present invention may be administered as a single dose or in multiple divided doses. Additionally, it is important that the least amount which can achieve the maximum effect without any side effects be administered in consideration of all the factors described above.

As used and described herein, the dose of the formulation of the present invention may be determined by a skilled person in the art considering the intended use(s), severity of disease(s), age, body weight, sex and anamnesis of a subject, or the kinds of ingredients used as active ingredient(s), etc. For example, the formulation of the present invention may be administered in the range of from about 0.3 g/kg/day to about 2.2 g/kg/day for mammals including humans, and preferably from 1 g/kg/day to 2 mg/kg/day. Where required, the formulation may be administered in amounts as high as 10 g/kg/day at the discretion of a skilled practitioner. The formulation of the present invention may be administered once daily or in a few divided doses, although administration is not particularly limited thereto. However, as described herein the method of the invention required the clinician to consider the specific parameters described herein to assure the dosage is optimized.

As used herein, the terms "curcuminoid" and "active curcuminoid" refer to species within the curcuminoid genera that is capable of inhibiting the inducibility and/or activity of COX-2 while having no or no effect on COX-1 or is capable of inhibiting or reducing the severity of an inflammatory response. The curcuminoid can be extracted from natural products or chemically synthesized.

As used herein, the term "extract" may refer to a product obtained from the listed ingredients used in the present invention by a conventional extraction method, or the product as such purchased commercially. Preferably, the extracts may be obtained using an extraction solvent such as water, ethanol or other non-toxic solvent extraction methodology. As used herein, the term "a mixture of extracts" refers to a resultant product obtained by combining each of the individual extracts of (list of ingredients). The mixture of extracts may be used in a formulation for preventing, treating, or ameliorating IBD.

As used herein, "fiber" refers to a fiber approved for human consumption. For example, in the US fiber would be defined as an FDA approved fiber, which can be found in the FDA approved list of fibers.

As used herein, the term "formulation" refers to the composition of the invention. The formulation may additionally contain micronutrients, such as vitamins, minerals, and the like.

As used herein, the term "functional food" or "medical food", is a nutrition support formula or composition, which is used in the treatment of a disease or support of a patient that may otherwise be suffering from disease or symptoms, even if healthy upon presentment to a medical professional. This term has the same meaning as the term "for special health use (FoSHU)", refers to a food with high effects in medicinal and medical treatment, modulating so as to efficiently exhibit a body modulating function as well as provide nutrients. The functional food may be manufactured in various forms including tablets, capsules, powders, granules, liquids, pills, etc., in order to obtain useful effects for the prevention or amelioratement of inflammatory bowel diseases. The composition is a nutritional support formulation or composition, and in some jurisdictions may be considered a functional food or a medical food. In the US, the term medical food, is defined in section 5(b) of the Orphan Drug Act (21 U.S.C. 360ee (b) (3)) is "a food which is formulated to be consumed or administered entirely under the supervision of a physician and which is intended for the specific dietary management of a disease or condition for which distinctive nutritional requirements, based on recognized scientific principles, are established by medical evaluation."

As used herein, the term "gastrointestinal tract" (and thus the associated abbreviation "GI tract") refers to an organ system within an animal (e.g. a mammal) that ingests foodstuff, digests the foodstuff (e.g. to extract and/or absorb nutrients from the foodstuff or components thereof), and expels any non-digested component(s) of the foodstuff as waste (e.g. as urine and/or feces). In certain instances, the terms "digestive tract", "GIT", "gut", and "alimentary canal" may be used synonymously to refer to a GI tract. A GI tract may comprise multiple organs and/or anatomic structures, such as a mouth, esophagus, stomach, and intestine(s). Moreover, as will be understood by one of skill in the art, a GI tract may be divided into multiple systems, such as upper and lower tracts, and small and large intestines. Each of such systems may comprise a number of anatomic structures, including a buccal cavity, pharynx, esophagus, stomach, duodenum, jejunum, ileum, cecum, colon(s) (e.g. ascending, transverse, descending, and sigmoid colons, and colic flexure(s)), rectum, and anus.

As used herein, the term "hop extract" refers to the solid material resulting from (1) exposing a hops plant product to a solvent, (2) separating the solvent from the hops plant products, and (3) eliminating the solvent.

As used herein, the term "inflammatory bowel disease (IBD)" refers to a disease that induces an inflammation in the gastrointestinal tract with accompanying symptoms such as abdominal pain, fever, diarrhea, and melena.

As used herein, the term "mammal" refers to an organism of the kingdom Animalia of the class Mammalia that has a gastrointestinal (GI) tract. All mammals have digestive tracts. Mammals that are specifically contemplated herein are domesticated mammals, such as dogs, cats, goats, sheep, pigs, cattle, horses, donkeys, camels, and the like. Additional mammals that are specifically contemplated herein include semi-domesticated mammals and mammals that are routinely bred in captivity. Of course, the term mammal also encompasses humans (which may be referred to as "people" and/or "person(s)." When describing a human, the term "adult" is typically used herein to refer to a human that has reached sexual maturity. By contrast, the terms "child" and "juvenile" are used herein to refer to a human that has not yet reached sexual maturity. Typically, the term "child" means a human subject between the stage of birth and the age of about 10 (i.e., childhood), and the term "juvenile" means a human subject that is greater than the age of about 10 and who has not completed the stage of puberty. Of course, the terms child, juvenile, adult, and infant are all encompassed by the term human, which is itself a subcategory of mammal, which is a subcategory of animal as defined herein.

As used herein, the term "prevention" refers to all kinds of activities associated with the inhibition, reduction of clinical symptoms or sequalae, or delay of inflammatory bowel diseases by administering the formulation of the present invention.

As used herein, regardless of the specific use in the examples herein, the term "subject" refers to any animal, including humans, having a risk of inflammatory bowel disease(s) or having inflammatory bowel disease(s). The administration of the formulation of the present invention can alleviate or treat the inflammatory bowel disease(s) of the subject.

As used herein, "Subject response", Subject responsiveness", "Patient response" or "patient responsiveness" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment. The term "responsiveness" refers to a measurable response, including complete response (CR) and partial response (PR).

Treatment," "treating," and grammatical variations thereof refer to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, and diminishment of any direct or indirect pathological consequences of the disease, decreasing the rate of disease progression, amelioration or palliation of the disease state, and remission or improved prognosis.

As used herein, "treatment regimen" refers to a combination of dosage, frequency of administration, or duration of treatment, with or without addition of a second medication. Thus, as used herein, an "Effective treatment regimen" refers to a treatment regimen that will offer beneficial response to a patient receiving the treatment. Thus, treatment refers to all kinds of activities associated with clinical intervention for the purpose of changing the clinical pathological state of an affected patient, whether the IBD is still in progress or to prevent the occurrence of the same. Examples of the aimed purposes of the therapeutic effects may include preventing occurrence or recurrence of a given disease, alleviating the symptoms therefrom, reducing all the direct or indirect pathological results due to the disease, decreasing the progress of the disease, reducing or temporarily alleviating and ameliorating the disease, or improving prognosis of the disease.

As used herein, all p-values are calculated using paired t-tests. The following abbreviations may be used in the text and in the examples herein: SD, standard deviation; $\Delta$, change; ng, nanogram; mL, milliliter; pg, pictogram; RBC, red blood cell; uL, microliter; g, gram; dL, deciliter; mmol, millimoles; L, liter; mg, milligrams; RDI, reference daily intake; g, grams; mg, milligrams; mcg, micrograms; IU, international units; SE, standard error; $\Delta$, change; GIGLI, Gastrointestinal Quality of Life Questionnaire; IBDQ, Inflammatory Bowel Disease Questionnaire (IBDQ).

A composition is provided for treatment of inflammation in a mammal. As introduced above, modulation of leukocyte subtypes may be indicative of a disease related to inflammation in mammals. For example, relative amounts of leukocyte subtypes, such as neutrophils and lymphocytes, may be determined for evaluating progression of disease. In certain embodiments, the mammal has a neutrophil to lymphocyte ratio (NLR) and 12 weeks after ingestion of the composition by the mammal results in a decrease in the NLR of the mammal.

In certain embodiments, the composition is formed of natural ingredients in a specific formulation and configuration and used in a specific regimen for the amelioration of IBD.

In various embodiments, a method for detecting, preventing or ameliorating IBD using the formulation is also provided. A further objective of the present invention is to provide a method for monitoring treatment using objective clinical measures, in addition to symptomology.

In other embodiments, a method for preventing or treating IBD is also provided. The method may include administering a pharmaceutically effective amount of the composition to a subject having a risk of developing an inflammatory bowel disease or having IBD.

In yet other embodiments, a regimen for administering the composition is provided for preventing or ameliorating IBD.

In still other embodiments, a method of predicting the response of a patient suffering from IBD to a therapy is provided.

The composition includes a curcumagalactomannoside and a hops extract. In various embodiments, the curcumagalactomannoside and the hops extract cooperate to decrease the NLR of the mammal 12 weeks after ingestion of the composition. The NLR of the mammal may decrease in an amount of from about 1% to about 70%, alternatively from about 5% to about 60%, or alternatively from about 8% to about 55%, 12 weeks after ingestion of the composition relative to the NLR of the mammal at ingestion. The curcumagalactomannoside may be present in the composition in an amount of from about 0.01 wt. % to about 10 wt. %, alternatively from about 0.05 wt. % to about 5 wt. %, or alternative from about 0.1 wt. % to about 1 wt. %, based on a total weight of the composition.

The curcumagalactomannoside is a derivative of a curcumin-containing compound. In certain embodiments the curcumin-containing compound is a curcuminoid. The curcumagalactomannoside may exhibit improved in vivo bioavailability and thus improved efficacy, relative to curcuminoids. In certain embodiments, the curcumagalactomannoside is derived from a curcuminoid and a galactomannan. The galactomannan may include a gel forming, non-digestive, soluble dietary polysaccharide fiber galactomannan and proteins derived from fenugreek (*Trigonella Foenum graecum*). In various embodiments, the curcuminoids of the curcumagalactomannoside are impregnated in a matrix including the galactomannan. The curcuminoid may be present in the curcumagalactomannoside in an amount of from about 20 wt. % to about 60 wt. %, alternatively from about 25 wt. % to about 55 wt. %, or alternatively from about 30 wt. % to about 50 wt. % based on a total weight of the curcumagalactomannoside.

A process for forming a curcumagalactomannoside including galactomannans and proteins derived from fenugreek (*Trigonella Foenum graecum*) may include forming a water dispersed colloidal dispersion of curcuminoids and fenugreek fiber by grinding or mixing the water dispersed colloidal dispersions under ultrasound mediated mixing (sonication), homogenization and the like, to produce a curcuminoid encapsulated fiber dispersions. Further sonication or homogenization may be carried out at 50° C. to form a uniform viscous solution of curcuminoids dispersed in a fiber gel phase of the galactomannan.

The curcumagalactomannoside may also be in the form of a colloidal curcumin encapsulated fiber dispersion as amorphous and water miscible microgranulates. The microgranulates may exhibit uniform size and density. The microgranulates of the curcumagalactomannoside may be formed by drying the curcuminoid encapsulated fiber dispersions described above under vacuum and below 80° C. and employing techniques such as rotary drying followed by granulation or spray drying.

The curcuminoid may be derived from dried rhizomes of turmeric that are powdered and extracted with a mixture of hexane and acetone and solvent. The hexane and acetone and solvent may be evaporated to form a pasty mass commonly known in the art as turmeric oleoresin. Other solvents, such as ethylalcohol, ethyl acetate, ethylene chloride, or mixtures thereof can also be used for the extraction. The turmeric oleoresin may then be dissolved in compositions of ethanol, isopropanol, or mixtures thereof to form a crystallize curcuminoid with a purity of from about 85 to about 95 wt. %. The crystallize curcuminoid may then be filtered and dried under vacuum at 70° C. The dried crystallize curcuminoid may then be pulverized to form curcumin powder with a purity of from about 85 to about 95 wt. % and an average particle size of from about 150 to about 250 microns. Purity may be determined by the method of JECFA 2003 method (Joint Expert Committee on Food Additives), by measuring the absorbance at 420 nm in acetone.

The soluble fiber galactomannan may be derived from fenugreek seeds. Briefly, matured fenugreek seeds may be flaked and successively extracted with ethanol to produce debittered and deodorized fenugreek seeds by removing the phytochemicals such as alkaloids, saponins, flavanoids etc. The flaked and extracted fenugreek seeds may then be dried to remove the solvent and subjected to differential grinding and sieving to separate the endosperm of fenugreek seeds containing the galactomannan fiber and proteins from the seed coat. White endosperm powder is then obtained and is dissolved in excess of water. The galactomannan fraction may then be precipitated along with proteins by the addition of calculated quantity of ethanol. The precipitate may then be filtered to arrive at a minimum of 80 wt. % soluble fiber content upon enzymatic-gravimetric analysis (AOAC 2000 ed., Enzymatic Gravimetric analysis of dietary fiber, Method No. 985.29) and a minimum of 5 wt. % protein content as determined by Kejndhal method.

The composition may further include a curcumin-containing compound or derivative thereof different from the curcumagalactomannoside. The curcumin-containing compound or derivative thereof may include, but is not limited to, curcumin, curcumagalactomannoside, demethoxycurcumin, bisdemethoxycurcumin, cis-trans-curcumin and cyclocurcumin.

The curcumin-containing compound or derivative thereof may be a yellow pigmented fraction isolated from the rhizomes of *Curcuma longa*. The rhizome contains curcuminoids belonging to the dicinnamoyl methane group. Curcuminoids are present to the extent of 3 to 5 percent. They are considered the most important active ingredients and are believed to be responsible for the biological activity of *Curcuma longa*. Though their major activity is anti-inflammatory, curcuminoids have been reported to possess antioxidant, anti-allergic, wound healing, antispasmodic, antibacterial, antifungal and antitumor activity as well. Curcumin was isolated in 1815 and structurally defined in 1910. Other curcuminoids isolated from *Curcum longa* include demethoxycurcumin, bisdemethoxycurcumin, a cis-trans geometrical isomer of curcumin, and cyclocurcumin. Curcuminoids may be found in other botanicals in addition to *Curcuma longa*, such as *Curcuma xanthorrhiza* and *Curcuma zedoaria*.

Curcuminoids are well known for their anti-inflammatory activity. Tumeric is one of the oldest anti-inflammatory drugs used in Ayurvedic medicine. The anti-inflammatory activity of curcuminoids has been evaluated in inflammatory reaction models such as chemical or physical irritants like carrageenin, cotton pellets, formaldehyde and the granuloma pouch. Human, double-blinded, clinical trials have demonstrated efficacy in rheumatoid arthritis at a dose of 1200 mg curcuminoids/day for five to six weeks. At these doses, however, signs of gastrointestinal (GI) discomfort and stomach irritation are frequently reported. The GI upset and stomach irritation caused by high doses of curcuminoids may be due to the fact that curcuminoids act on prostaglandin production in a manner similar to that of aspirin and aspirin-like anti-inflammatory agents.

In various embodiments, the curcuminoid is a pharmaceutical grade botanical extract such as can be obtained commercially, for example, from Sabinsa (121 Ethel Road West, Piscataway, N.J.). The curcuminoid used can be readily obtained from *Curcuma longa* L. Pharmaceutical grade curcuminoid extract is standardized to have a curcuminoid content of greater than about 70 percent. The pharmaceutical, botanical grade extract can be assayed for safety and efficacy. As employed in the embodiments of the invention, the extract has a curcuminoid content of about 1 to 99 percent by weight. The minimum curcuminoid content is generally about 70 percent by weight, and can be, for example, at least about 75%, at least about 80%, at least about 85%, at least about 90%, at least about 95%, or greater. Alternatively, the curcuminoid may be synthesized using standard techniques known in chemical synthesis.

As introduced above, the composition further includes the hops extract. The hops extract may also reduce inflammation. Hop extraction may be performed with ethanol or organic solvent extracts (for example, hexane) and $CO_2$ extracts (supercritical and liquid). $CO_2$ (typically at 60 bars pressure and 50 to 10° C.) is in a liquid state and is a relatively mild, non-polar solvent highly specific for hop soft resins and oils. Beyond the critical point, typically at 300 bars pressure and 60° C., $CO_2$ has the properties of both a gas and a liquid and is a much stronger solvent. The composition of the various extracts is compared in Table 1.

At its simplest, hop extraction involves milling, pelleting and re-milling the hops to spread the lupulin, passing a solvent through a packed column to collect the resin components and finally, removal of the solvent to yield a whole or "pure" resin extract.

TABLE 1

Components of a hop extract (wt. %)

| Component | Hops | Organic Solvent | Super-Critical $CO_2$ | Liquid $CO_2$ |
|---|---|---|---|---|
| Total resins | 12-20 | 15-60 | 75-90 | 70-95 |
| Alpha-acids | 2-12 | 8-45 | 27-55 | 30-60 |
| Beta-acids | 2-10 | 8-20 | 23-33 | 15-45 |
| Essential oils | 0.5-1.5 | 0-5 | 1-5 | 2-10 |
| Hard resins | 2-4 | 2-10 | 5-11 | None |
| Tannins | 4-10 | 0.5-5 | 0.1-5 | None |
| Waxes | 1-5 | 1-20 | 4-13 | 0-10 |
| Water | 8-12 | 1-15 | 1-7 | 1-5 |

The main organic extractants are strong solvents and in addition to virtually all the lupulin components, they extract plant pigments, cuticular waxes, water and water-soluble materials.

Supercritical $CO_2$ is more selective than the organic solvents and extracts less of the tannins and waxes and less water and hence water-soluble components. It does extract some of the plant pigments like chlorophyll but rather less than the organic solvents do. Liquid $CO_2$ is the most selective solvent used commercially for hops and hence produces the most pure whole resin and oil extract. It extracts hardly the hard resins or tannins, much lower levels of plant waxes, no plant pigments and less water and water-soluble materials.

As a consequence of this selectivity and the milder solvent properties, the absolute yield of liquid $CO_2$ extract per unit weight of hops is less than when using the other mentioned solvents. Additionally, the yield of alpha acids with liquid $CO_2$ (89-93%) is lower than that of supercritical $CO_2$ (91-94%) or the organic solvents (93-96%). Following extraction, there is the process of solvent removal, which for organic solvents involves heating to cause volatilization. Despite this, trace amounts of solvent do remain in the extract. The removal of $CO_2$, however, simply involves a release of pressure to volatize the $CO_2$.

Hops $CO_2$ extracts can be fractionated into components, including hops oils, beta acids, and alpha acids. Hops oils include, but are not limited to, humulene, beta-caryophyllene, mycrene, farnescene, gamma-cadinene, alpha-selinene, and alpha-cadinene. Beta acids include, but are not limited to, lupulone, colupulone, adlupulone, tetrahydroisohumulone, and hexahydrocolupulone, collectively known as lupulones. Beta acids can be isomerized and reduced. Beta acids are reduced to give tetra-beta acids. Alpha acids include, but are not limited to, humulone, cohumulone, adhumulone, hulupone, and isoprehumulone. Alpha acids can be isomerized to give isoalpha acids. Iso-alpha acids can be reduced to give reduced-isoalpha acids, tetra-hydroisoalpha acids, and hexa-hydroisoalpha acids.

The identification of humulone from hops extract as an inhibitor of bone resorption is reported in Tobe et al. (*Biosci. Biotech. Biochem* 61(1):158-159 (1997)). Later studies by the same group characterized the mechanism of action of humulone as inhibition of COX-2 gene transcription following TNFalpha stimulation of MC3T3, E1 cells (Yamamoto, *FEBS Letters* 465:103-406 (2000)). It was concluded that the action of humulone (also humulon) was similar to that of glucocorticoids, but that humulone did not function through the glucocorticoid receptor. While these results establish that humulone inhibits $PGE_2$ synthesis in MC3T3 cells (osteoblasts) at the gene level, one skilled in the art would not assume that these results would necessarily occur in immune inflammatory cells or other cell lines. As disclosed herein, hops compounds and derivatives exhibit a high degree of tissue selectivity in target and non-target cell. Furthermore, the hops derivatives described in the present invention are structurally distinct from the alpha acid humulone.

In various embodiments, the hops extract includes at least one fraction isolated or derived from hops (*Humulus lupulus*). Examples of fractions isolated or derived from hops are alpha acids, isoalpha acids, reduced isoalpha acids, tetrahydroisoalpha acids, hexa-hydroisoalpha acids, beta acids, and spent hops. Fractions isolated or derived from hops, include, but are not limited to, xanthohumol, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. In certain embodiments, compounds can also bear substituents, such as halogens, ethers, and esters. In various embodiments, the hops extract includes xanthohumol. The hops extract may be present in the composition in an amount of from about 0.01 wt. % to about 10 wt. %, alternatively from about 0.05 wt. % to about 5 wt. %, or alternatively from about 0.1 wt. % to about 1 wt. %, based on a total weight of the composition.

Compounds of the fractions isolated or derived from hops can be represented by a supragenus below:

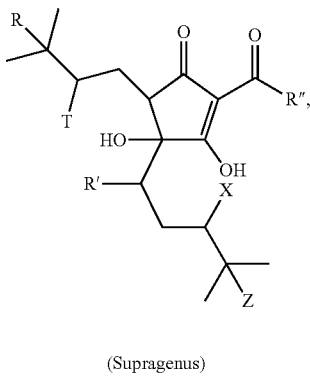

(Supragenus)

wherein R' is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In another embodiment, compounds of the fractions isolated or derived from hops can be represented by a genus below:

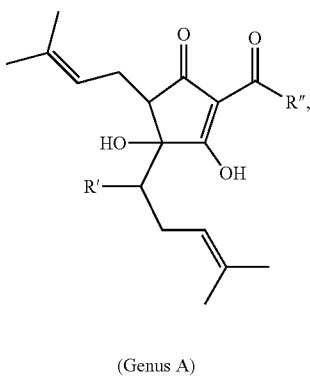

(Genus A)

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$. Exemplary Genus A structures include isoalpha acids such as isohumulone, isocohumulone, isoadhumulone, and the like, and reduced isoalpha acids such as dihydro-isohumulone, dihydro-isocohumulone, dihydro-isoadhumulone, and ether or ester conjugates or halogenated modifications of the double bond.

In yet another embodiment, compounds of the fractions isolated or derived from hops can be represented by a genus below:

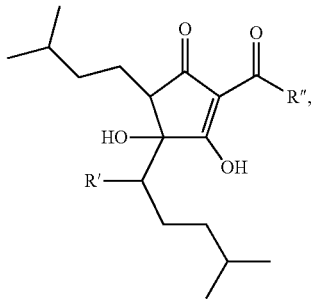

(Genus B)

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$. Exemplary Genus B structures include tetra-hydroisoalpha acids such as tetra-hydro-isohumulone, tetra-hydro-isocohymulone and tetra-hydro-adhumulone, and the like, and hexa-hydroisoalpha acids such as hexa-hydro-isohumulone, hexa-hydro-isocohumulone and hexa-hydro-isoadhumulone, and ether or ester conjugates.

Examples of compounds of an ingredient isolated or derived from hops, include, but are not limited to, humulone, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. The compounds can bear substituents, as shown in the formula above.

Hops derivatives are known compounds occurring naturally in plants and found in food products and beverages. They may be prepared by any of the extraction and processing methods known in the art. Hops derivatives can be prepared directly from plant material in any known manner. The hops derivatives may be purified by methods known in the art, for example, by recrystallization from aqueous organic solvents such as aqueous alcohols. Synthetic modifications of hops derivatives may be prepared according to methods known in the pharmaceutical art of drug modification.

The composition may further include a protein-containing matrix. The protein-containing matrix may include the hops extract. The hops extract may be present in the protein-containing matrix in an amount of from about 1 to about 95 wt. %, based on a total weight of the protein-containing matrix. In certain embodiments, the protein-containing matrix may be a rice protein matrix with polyphenols from the hops contained therein. The polyphenols may include xanthohumol. The xanthohumol may be present in the protein-containing matrix in an amount of from about 0.1 to about 10 wt. %, alternatively from about 1 wt. % to about 10 wt. %, or alternatively from about 1 wt. % to about 5 wt. %, based on a total weight of the protein-containing matrix.

In various embodiments, the composition may further includes a ginger root extract. The ginger root extract may be derived from ginger (e.g., *Zingiber officinalis*). The ginger root extract may include a pungent compound, including phenylalkylketones (gingerols, shogaols, and zingerone) and volatile oils (zingiberone, bisabolene, camphene, geraniol, linalool, and borneol). Ginger provides benefits when treating indigestion and flatulence, and it has a broad range of action against intestinal parasites. Gingerols and other active ingredients in ginger provide beneficial anti-inflammatory properties and reductions in blood platelet clumping. Gingerols are compounds that also inhibit 5-lipoxygenase in humans, and therefore reduce biosynthesis of certain inflammatory thromboxanes. See Kiuchi F., Iwakami S., Shibuya M., Hanaoka F., Sankawa U., Inhibition of prostaglandin and leukotriene biosynthesis by gingerols and diarylheptanoids, Chem. Pharm. Bull. (Tokyo) 1992 February; 40(2):387-391. In other embodiments, the composition may include an effective amount of gingerol with the gingerol being derived from a botanical source. The ginger root extract may include the pungent compound in an amount of from about 0.1 to about 20 wt. %, alternatively from about 1 to about 10 wt. %, or alternatively from about 3 to about 7 wt. %, based on a total weight of the ginger root extract.

Ginger provides additional anti-inflammatory benefits. The anti-inflammatory effects of ginger are reportedly attributable to the presence of gingerols. It is also reported that the active components of ginger inhibit cyclooxygenase and 5-lipoxygenase activity in a manner that inhibits biosynthesis of prostaglandin E2 (PGE-2) and leukotriene B4 (LTB4), respectively. See Srivastava K. C., Mustafa T., Med Hypotheses 1992, "Ginger (*Zingiber officinale*) in rheumatism and musculoskeletal disorders," December; 39 (4):342-348, Department of Environmental Medicine, Odense. University, Denmark. The inhibitory effects of the active components of ginger on cyclo-oxygenase activity, a key enzyme system required for biosynthesis of prostaglandins, which are active in the etiology of acute and chronic inflammation as well as cytoprotection of the gastric mucosa, is expected to be confirmed in the future. Anti-platelet activity and inhibition of thromboxane synthetase (5-lipoxygenase) are the most likely mechanisms proposed to explain the observed biological activity of ginger as an antiinflammatory agent. See Guh J. H., Ko F. N., Jong T. T., Teng C. M., "Antiplatelet effect of gingerol isolated from *Zingiber officinale*," J Pharm Pharmacol 1995 April; 47(4):329-332; Kiuchi F., Iwakami S., Shibuya M., Hanaoka F., Sankawa U., "Inhibition of prostaglandin and leukotriene biosynthesis by gingerols and diarylheptanoids," Chem Pharm Bull (Tokyo) 1992 February; 40(2):387-391. The ginger root extract may be present in the composition in an amount of from about 0.01 wt. % to about 10 wt. %, alternatively from about 0.05 wt. % to about 5 wt. %, or alternatively from about 0.1 wt. % to about 1 wt. %, based on a total weight of the protein-containing matrix.

The composition may further include a citrus bioflavonoid. Citrus bioflavonoids include quercetin, isoquercetin, hesperidin, rutin, naringen, naringenin, and limonene. In certain embodiments, the citrus bioflavonoid includes quercetin. Quercetin is a natural reverse transcriptase blocker commonly found in red apples and red onions. Quercetin has been shown to have antiviral activity against HIV, herpes simplex, and the respiratory syncytial virus. Raul, T. N. Middleton E., & Ogra P. L. "Antiviral effects of flavonoids on human viruses," J Med Virol, 15: 71-79, 1985 and Vrijsen, R., Everaert, & Boeye A. "Antiviral activity of flavones and potentiation by ascorbate," J Gen Virol 69: 1749-51, 1988.

Isoquercetin is a common flavonoid found in onions, apples, *Arnica* species, *Gossypium arboreum, Ginko biloba, Ricinus communis, Ocimum basilicum, Salix acutifolia*, and *Narcissus pseudonarcissus*. Rich dietary sources of quercetin are onions, apples, kale, sweet cherries, grapes, red cabbage, and green beans. Hesperidin is found in the rinds of oranges and lemons. It helps strengthen capillary walls in conjunction with vitamin C. Naringen is found in grapefruit and is responsible for most of grapefruit's bitter taste. Other bioflavonoids include: isoflavones, proanthocyanidins, anthocyanidins, ellagic acid, catechin, and tannin.

Isoquercetin shares the same aglycone with rutin and quercitrin: quercetin. It has been shown that quercetin-containing glycosides liberate quercetin in the intestinal tract. Therefore, it is justified to assume that all the pharmacological properties of quercetin are also shared by isoquercetin and rutin when administered orally. Recent investigation demonstrated a rapid absorption of isoquercetin and quercetin-glucosides by the sodium-dependent glucose transport pathway in the small intestine. Due to superior bioavailability, the health effects of isoquercetin are increased compared to other flavonoids. Isoquercetin is known to have anti-inflammatory activity without adverse effects on the gastrointestinal tract, such as those caused by NSAIDs. Isoquercetin further exhibits beneficial effects as an antioxidant, antihypertensive, anticarcinogenic, antimicrobial, and analgesic agent.

Flavonoids (also called bioflavonoids) are natural botanical pigments that provide protection from free-radical damage, among other functions. Bioflavonoids provide protection from damaging free radicals and are believed to reduce the risk of cancer and heart disease, decrease allergy and arthritis symptoms, promote vitamin C activity, improve the strength of blood vessels, block the progression of cataracts and macular degeneration, treat menopausal hot flashes, and other ailments. Flavonoids occur in most fruits and vegetables. It is believed that flavonoids act by inhibiting hormones, such as estrogen, that may trigger hormone-dependent malignancies like cancers of the breast, endometrium, ovary, and prostate.

Studies show that quercetin can block the spread of cancer cells in the stomach. Flavonoids also stabilize mast cells, a type of immune cell that releases inflammatory compounds, like histamine, when facing foreign microorganisms. Histamine and other inflammatory substances are involved in allergic reactions. Mast cells are large cells present in connective tissue. Flavonoids fortify and repair connective tissue by promoting the synthesis of collagen. Collagen is a remarkably strong protein of the connective tissue that "glues" the cells together. Flavonoids are believed to benefit connective tissue and reduce inflammation.

The composition may further include rosemary, rosemary extract, or those compounds known to be found in rosemary or extracts of rosemary. These include 1,8-cineole, 19-alpha-hydroxyursolic acid, 2-β-hydroxyoleanolic acid, β-O-acetyloleanolic acid, β-O-acetylursolic acid, 6-methoxy-luteolin-7-glucoside, 6-methoxyluteolin, 6-methoxyluteolin-7-glucoside, methoxyluteolin-7-methylether, 7-ethoxy-rosmanol, 7-methoxy-rosmanol, alpha-amyrin, alpha-humulene, alpha-hydroxyhydrocaffeic acid, alpha-pinene, alpha-terpinene, alpha-terpinenyl acetate, alpha-terpineol, alpha-thujone, apigenin, apigenin-7-glucoside, curcumene, benzyl-alcohol, β-amyrenone, β-amyrin, β-elemene, β-pinene, botulin, betulinic acid, borneol, bornyl-acetate, caffeic acid, camphene, camphor, carnosic acid, carnosol, carvacrol, carvone, caryophyllene, caryophyllene-oxide, chlorogenic acid, diosmetin, gamma-terpinene, hesperidin, isoborneol, limonene, luteolin, luteolin-3'-O-(3"-O-acetyl)-β-D-glucuronide, luteolin-3'-O-(4"-O-acetyl)-13-D-glucuronide, luteolin-3'-O-β-D-glucuronide, luteolin-7-glucoside, methyl-eugenol, myrcene, neo-chlorogenic acid, nepetin, octanoic acid, oleanolic acid, p-cymene, piperitenone, rosmanol, rosmaric acid, rosmaricine, rosmaridiphenol, rosemarinic acid, rosmarinol, rosmariquinone, sabinene, sabinyl acetate, salicylates, salicylic acid-2-β-D-glucoside, squalene, terpinen-4-ol, terpinolene, thymol, trans-anethole, trans-carveol, ursolic acid, verbenone, and zingiberene. The composition may include the rosemary extract in an amount of from about 0.01 wt. % to about 10 wt. %, alternatively from about 0.05 wt. % to about 5 wt. %, or alternatively from about 0.1 wt. % to about 1 wt. %. [Please provide weight percent of rosemary extract in the composition]

The composition may include one or more additional components. Examples of suitable additional components include fat and/or lipid components, protein components, and additive components.

In certain embodiments, the composition includes a fat and/or lipid component. The fat and/or lipid component comprises fats (e.g. saturated, monounsaturated, polyunsaturated, and/or unsaturated) and/or lipids (e.g. cholesterol, other sterols). In certain embodiments, the fat and/or lipid component comprises sunflower oil, flaxseed oil, medium chain triglycerides, or a combination thereof. The composition may comprise the fat and/or lipid component in any suitable amount. In certain embodiments, the composition includes the fat and/or lipid component in an amount of from about 12.5 to about 30 wt. %, based on the total weight of the composition.

In some embodiments, the composition includes a protein component. The protein component typically includes a protein source, such as individual amino acids, peptides, oligopeptides, and/or proteins. In certain embodiments, the protein component includes pea protein isolate and/or rice protein concentrate. In these or other embodiments, the protein component comprises L-alanyl-L-glutamine, L-alanine, L-arginine, L-aspartic acid, L-cystine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-Valine, selenomethionine, or a combination thereof.

In various embodiments, the composition includes the protein component in an amount of from about 25 wt. % to about 75 wt. %, or alternatively from about 35 wt. % to about 50 wt. %, based on the total weight of the composition.

In other embodiments, the composition includes an additive component comprising one or more additive suitable for use in a composition. The additive component may comprise the fat and/or lipid component and/or the protein component, as each described above. Alternatively, the additive component may be separate from the fat and/or lipid component and/or the protein component, if present within the composition. As such, it is to be appreciated that composition may comprise one or more of the fat and/or lipid component, the protein component, and the additive component. In embodiments where each of such components is present in the composition, the additive component may comprise an amino acid, a peptide, and/or a protein that is the same as or different than any one or more amino acid, peptide, and/or protein present in the protein component. Likewise, the additive component may comprise a fat and/or lipid that is the same as or different than any fat and/or lipid present in the fat and/or lipid component. As such, the ranges listed herein with respect to the any particular component may encompass the total amount of such component (e.g. the protein, lipid, and/or additive components) present within the composition, or may refer merely to amount of a single, particular component described therewith.

Examples of suitable additives for use in the additive component include amino acids, peptides, proteins, lipids, vitamins, carbohydrates, nucleic acids, minerals, anabolic nutrients, antioxidants, probiotic bacterial strains, lipotropic agents, extracts, concentrates, oils, gums, and combinations thereof. In certain embodiments, the composition comprises the additive component, and the additive component comprises an amino acid, a peptide, a protein, a lipid, a vitamin, a carbohydrate, a nucleic acid, a mineral, an anabolic nutrient, an antioxidant, a probiotic bacterial strain, a lipotropic agent, or any combination thereof. In these or other embodiments, the additive component comprises a flavoring agent, a dye, a flow modifier, a preservative, a filler, a binder, a dispersing agent, a carrier, a supplemental nutrient, or any combination thereof. In certain embodiments, the additive component comprises a carrier, such as a consumable, nutritional, and/or pharmaceutical carrier, or a combination thereof.

In various embodiments, the composition includes at least one additive component to improve usefulness of the composition to a patient experiencing malnutrition as a result of IBD and to improve palatability. The at least one additive may include (i) an amino acid; (ii) a peptide; (iii) a protein; (iv) a lipid; (v) a vitamin; (vi) a carbohydrate; (vii) a nucleic acid; (viii) a mineral; (ix) an anabolic nutrient; (x) an antioxidant; (xi) a probiotic bacterial strain; (xii) a lipotropic agent; (xiii) a flavoring agent; (xiv) a dye; (xv) a flow modifier; (xvi) a preservative; (xvii) a filler; (xviii) a binder; (xix) a dispersing agent; (xx) a prebiotic, (xxi) isomalto-oligosaccharide (IMO); (xxii) human milk oligosaccharide(s), including but not limited to 2'fucosyllactose (2'FL), 6'sialyllactose (6'SL), or 3'sialyllactose (3'SL): or any combination of the ingredients described above.

In addition to those additives listed above, specific examples of additives suitable for use in the additive component include pea protein isolate, isomalto-oligosaccharide (IMO), rice protein concentrate, 2'-fucosyllactose powder, flaxseed, organic cane sugar, natural flavors, high oleic sunflower oil, L-lysine HCl, medium chain triglycerides, L-leucine, Silica, L-valine, L-alanyl-L-glutamine, L-isoleucine, xanthan gum, vitamins, minerals, zinc gluconate, ascorbic acid, manganese gluconate, alpha tocopheryl acetate, copper gluconate, D-biotin, retinyl palmitate, niacinamide, cholecalciferol, calcium pantothenate, chromium picolinate, pyridoxine HCl, riboflavin, potassium iodide, thiamin HCl, calcium L-5-methyltetrahydrofolate, selenomethionine, and methylcobalamin, Luo Han Guo fruit (monk fruit) extract, vanilla, cocoa powder, vitamin E, thiamin, riboflavin, niacin, vitamin B6, folate, vitamin B12, biotin, pantothenic acid, phosphorus, iodine, magnesium, zinc, selenium, copper, manganese, and the like, and combinations thereof.

In various embodiments, the composition includes the additive component in an amount of from about 12.5 to about 75, alternatively from about 17.5 to about 75, alternatively from about 17.5 to about 50, alternatively from about 25 to about 50, alternatively from about 25 to about 45, alternatively from about 35 to about 50, alternatively from about 35 to about 45, alternatively of 17.5, 25, 35, 45, or 50 wt. %, based on the total weight of the composition.

In other embodiments, another composition for treatment of inflammation in the mammal is provided. The composition consists essentially of the curcumagalactomannoside, the hops extract, the ginger root extract, the protein-containing matrix, the rosemary extract, folate, vitamin B-12, and quercetin, wherein at least the curcumagalactomannoside and the hops extract cooperate to decrease the NLR of the mammal 12 weeks after ingestion of the composition.

The composition may compose any form, such as a dry powder, a solution, a suspension, an emulsion, or the like. In certain embodiments, the composition is a dry powder. In some embodiments, the composition is adapted to be consumed as a liquid. For example, the composition may be a dry powder that is combined with a consumable liquid (e.g. water) to form a consumable liquid solution, suspension, or emulsion comprising the composition. Likewise, the composition may be adapted to be mixed with a foodstuff or beverage. As such, in some embodiments, the composition is, alternatively is a component of, a foodstuff or beverage. In these or other embodiments, the composition may be further defined as a food additive. Accordingly, it is to be appreciated that certain aspects of the present embodiments include the use of the composition as a food additive, and the use of the composition in methods of preparing foodstuff and/or beverages.

As introduced above, the present embodiments can include a foodstuff or beverage comprising the composition. The foodstuff or beverage is typically suitable for use in methods of reducing or suppressing inflammation in an animalian GI tract or a cause or symptoms thereof, such as diarrhea, inflammatory bowel disease (IBD), Crohn's disease, enterocolitis, ulcerative colitis, allergic colitis, irritable bowel syndrome, pouchitis, post-infection colitis, *Clostridium difficile*-associated diarrhea, Rotavirus-associated diarrhea, post-infective diarrhea, and/or diarrheal disease due to an infectious agent (e.g. *E. coli*), IBS, Celiac disease, intolerances, allergies, and combinations thereof.

Typically, the foodstuff or beverage comprises an admixture of the composition with one or more feed products, liquids, supplements, or combinations thereof. In particular embodiments, the foodstuff or beverage comprises 40 g of the composition per serving/unit dose of the foodstuff or beverage. However, in certain embodiments the composition may itself be further defined as a foodstuff or beverage composition, depending on the quantity, nature, and identity of individual additives and components present in the composition, such as those described above. Thus, it is to be appreciated that the embodiments described herein with respect to the composition are intended to equally encompass the foodstuff or beverage, a food or beverage product, and/or a food supplement comprising the composition. For example, in certain embodiments, the foodstuff or beverage comprising the composition comprises a fat and/or lipid component, a protein component, an additive component, or a combination thereof. As such, it is to be appreciated that any amount of fat and/or lipids, protein (e g amino acids, peptides, protein, etc.), and additives present in the composition will thus also be present in the foodstuff or beverage comprising the composition. Accordingly, any amounts and/or examples of such components described herein with respect to the composition itself may equally apply to the foodstuff or beverage comprising the composition, as will be understood by one of skill in the art.

Typically, the foodstuff or beverage comprising the composition comprises from 5 to 12 grams of fat components, if any, from 5 to 12 grams of lipid components, if any, and from 10 to 30 grams of protein components, if any, each based on a 40 gram dry weight sample of the foodstuff or beverage.

In some embodiments, the foodstuff or beverage comprising the composition is further defined as a nutritional composition. The nutritional composition typically has a nutritional value of at least 1 kilocalorie (kcal) per 100 grams (g) for dry food formulations (i.e., foodstuffs), or per 100 milliliters (ml) for liquid formulations (i.e., beverages). In certain embodiments, the nutritional composition has a nutritional value of at least 10, alternatively at least 50, alternatively at least 100, alternatively at least 300, kcal per 100 g for dry food formulations (i.e., foodstuffs), or per 100 ml for liquid formulations (i.e., beverages). In at least one embodiment, the nutritional formulation has a nutritional value of from 50 to 200 kcal/100 ml for liquid formulations, and of from 300 to 600 kcal/100 g for dry food formulations. In these or other embodiments, the nutritional composition is in the form of a dry food concentrate, which may be mixed with liquid or food and subsequently consumed. It is to be appreciated that the nutritional composition is distinguished from a vaccine, and the compositions described herein may be free, alternatively substantially free, from a vaccine.

In addition to the components described above with respect to the composition and the foodstuff or beverage comprising the composition, the nutritional composition may further comprise ingredients selected from lipids, minerals, carbohydrates, amino acids, amino acid chelates, anabolic nutrients, vitamins, antioxidants, probiotic bacterial strain, lipotropic agents, and the like, which may each be independently selected in order to provide the nutritional composition with a formulation capable of sustaining energy and/or anabolism in an animal.

In certain embodiments, the nutritional composition may be further defined as a nutritional supplement, or as a complete nutritive. For example, the nutritional composition may be formulated to provide a mammal (e.g. a human), via consumption of the nutritional composition, with at least 5%, alternatively at least 10%, alternatively at least 25%, alternatively at least 50%, alternatively at least 75%, alternatively at least 90%, of daily calories required by the mammal. However, it is to be appreciated that a daily calorie requirement is dependent on several factors, including the gender, height, and/or age of the mammal, and thus the percentage of caloric requirement provided by the nutritional composition will be dependent on the particular person consuming the nutritional composition. For example, a 30 year old human male of 80 kg body weight and 180 cm height has a daily calorie requirement of around 2900 cal (calories) to maintain his body weight whereas a 30 year old human female of 55 kg body weight and 165 cm height has a daily calorie requirement of around 2100 cal to maintain her body weight. In at least one embodiment, the nutritional formulation is a nutritional product for human infants or juveniles.

In certain embodiments, the foodstuff or beverage is further defined as an animal food. In such embodiments, the foodstuff or beverage is typically formulated for ingestion by one or more non-human animals, such as livestock including cattle, swine, horses, sheep, goats, poultry, and fish, domesticated companionship species such as dogs, cats, fish, and rodents, undomesticated wildlife such as deer, moose, elk, migratory, and non-migratory fowl, those non-human animals described herein, and combinations thereof.

In some embodiments, the foodstuff or beverage is further defined as a medical food. As such, it is to be appreciated that the medical food comprises the composition, and may be the same as or different from the nutritional composition described above.

In certain embodiments, the composition and the medical food are formulated such that a 40 g dry weight serving of the medical food contains the lipid component in an amount of from 5 to 12 g, alternatively of 7 g. In these or other embodiments, the medical food is formulated such that a 40 g dry weight serving of the medical food contains the protein component in an amount of from 10 to 30 g, alternatively of from 15 to 20 g, alternatively of 18 g.

As introduced above, the present embodiments can provide a kit presentation, comprising a combination of the composition a pharmaceutical agent, for use in a method of reducing or suppressing inflammation in an animalian GI tract.

The kit presentation comprising the composition the pharmaceutical agent may be configured, and thus used, for providing separate, sequential, or simultaneous administration of the composition and the pharmaceutical agent, or a treatment comprising the pharmaceutical agent. Accordingly, the composition and the pharmaceutical agent may be formulated together in standard pharmaceutical dosage forms known in the art.

A method of treatment of inflammation in the mammal is also provided. The method includes obtaining a parameter of the mammal. The parameter includes a neutrophil level, a lymphocyte level, neutrophil to lymphocyte ratio (NLR), a mean red cell distribution of width, or combinations thereof. In certain embodiments, the parameter includes the NLR and the curcumagalactomannoside and the hops extract cooperate to decrease the NLR of the mammal 12 weeks after ingestion of the composition.

The method further includes dosing the composition based on the parameter. The method further may further include obtaining a parameter of the mammal after administration of the composition after a pre-determined amount of time. In certain embodiments, the pre-determined amount of time is from about 3 weeks to about 12 weeks. In various embodiments, the inflammation is related to inflammatory bowel disorder, Crohn's disease, ulcerative colitis, or combinations thereof.

A further embodiment includes the use of the composition in a method of preventing and/or treating a GI condition in an animal. The composition described herein has surprisingly been found to be useful in a method of, or as a therapeutic for, preventing, treating, and/or reducing GI (e.g. intestinal) inflammation associated with GI conditions.

Accordingly, in some embodiments, the composition is useful in a method of preventing and/or treating a GI condition in an animal (e.g., a mammal, a human) In these or other embodiments, the composition is useful in a method of prophylactically treating a GI condition. More specifically, in certain embodiments, the compositions described herein is administered to treat an individual suffering from any of a number of diseases or medical conditions characterized by or associated with GI inflammation, such as IBS, IBD, UC, Crohn's disease, diarrhea, constipation, diabetes, hypertension, dyslipidemia, obesity, heart disease, stroke, and those other conditions described above, or a combination thereof. In these or other embodiments, the composition is administered to treat (e.g. prophylactically) an individual who has undergone surgical intervention (e.g. removal of all or part of the individual's GI tract, such as an ileocecal valve, etc.).

Typically, the method of preventing and/or treating the GI condition in the animal comprises administering the composition to the animal (i.e., using the composition) to prevent, reduce, or eliminate symptoms and/or causes of one or more GI conditions. For example, in particular embodiments the composition is used to prevent and/or treat IBS, IBD, Celiac disease, Ulcerative colitis, Crohn's disease, or a combination thereof. However, in certain embodiments, preventing and/or treating the GI condition comprises healing or restoring health to a GI tract of the animal, reducing or suppressing inflammation in the GI tract of the animal, restoring a GI function in the animal, reducing an amount of a pathogen present in a large intestine of the animal, improving or enhancing a quality of life of the animal, or a combination thereof. As such, in certain embodiments, the method of preventing and/or treating the GI condition in the animal using the composition may be further defined as a synergistic method of healing, assisting in the health of, restoring the health of, or an adjunct therapy for, the GI condition.

In various embodiments, preventing and/or treating the GI condition comprises improving or enhancing the quality of life of the animal. In some such embodiments, the animal is a human and the method of preventing and/or treating the GI condition comprises improving or enhancing the quality of life of the human on a basis of a validated quality of life questionnaire, such as the Digestive Symptom Frequency Questionnaire (DSFQ), the Gastrointestinal Quality of Life Index (GIQLI), and/or the Inflammatory Bowel Disease Questionnaire (IBDQ), regardless of which GI condition is present.

It is to be appreciated that the composition may be administered to the animal by any means known in the art, including via topical, enteral, or parenteral routes. Typically, the composition is administered orally. However, rectal and/or enteral administration may also be used.

A further embodiment includes the use of the composition in a method of providing nutritional support in combination with a therapy to a host afflicted by a GI condition. The method includes administering the therapy and administering the composition as described above. The therapy may be any therapy and/or treatment for the GI condition. The composition may be administered to the host as a stand-alone composition, or as one or more of the foodstuff, beverage, nutritional composition, medical food, and kit presentation described above. In certain embodiments, the method of providing nutritional support in combination with the therapy further comprises administering a vitamin and/or mineral supplement to the host.

In certain instances, administering the composition to a host in accordance with the method described above may result in an increased yield in one or more host-derived commodity, such as eggs, meat, milk, wool, or combinations thereof.

The composition may be administered as needed, daily, several times per day or in any suitable regimen such that the desired outcome is achieved. In the methods, the frequency of administration can depend on several factors, including the desired level of prevention and/or treatment. Generally, a regimen includes administration of the composition to the host once or twice daily to include an administration in the morning and/or an administration in the evening. The amount of composition administered to the host during each administration may depend on several factors including level of desired results and the specific composition.

Additional Embodiments

The following additional embodiments are provided, the numbering of which is not to be construed as designating levels of importance. Moreover, it is to be understood that the embodiments recited below are provided in conjunction with and in addition to the embodiments described above, as well as those claimed further below. Thus, it is also to be understood that variations, combinations, and/or modifications of the embodiment(s) and/or features of the embodiment(s) may be within the scope of the present invention.

Likewise, alternative embodiments that result from combining, integrating, and/or omitting features of the embodiment(s) described herein may also be within the scope of the present invention.

Embodiment 1 relates to a method of treatment of IBD comprising administering the formulation comprising curcumin as curcumagalactomannoside (preferably a mixture of curcuminoids from turmeric root/*Curcuma longa* and galactomannans from fenugreek/*Trigonella foenum-graecum* seed fiber, having about 40% curcuminoids), hops/ *Humulus lupulus* extract (having about 2.5% xanthohumol in a protein matrix), ginger root/*Zingiber officinale* extract, rosemary leaf/*Rosmarinus officinalis* extract, folate, vitamin B12 and quercetin, defined as Formula X.

Embodiment 2 relates to the method of embodiment 1, wherein the dosage for the Formula X is adjusted by taking into account the parameters measured herein, wherein the parameters measures are Neutrophil levels, Lymphocyte levels, the neutrophil/lymphocyte ratio, and the mean red cell distribution of width, in accordance with the levels and thresholds shown herein.

Embodiment 3 relates to the method of embodiments 1 or 2, wherein the dosage for the Formula X is adjusted by taking into account the parameters measured herein, wherein the parameter's measures are Neutrophil levels, Lymphocyte levels, the neutrophil/lymphocyte ratio, and the mean red cell distribution width, and wherein the dosage of the formulation of Formula X begins as a partial dosage that is increased incrementally based on patient tolerance, wherein, highly-sensitive or highly-symptomatic individuals begin taking a half a scoop once on the first day that they begin Formula X, and dosage increases incrementally until a full dosage, preferably two full scoops twice per day is reached, based on tolerability.

Embodiment 4 relates to the method of any one of embodiments 1 to 3, wherein symptoms are taking into account via a quality of life/symptom questionnaire.

Embodiment 5 relates to the method of any one of embodiments 1 to 4, wherein the parameters are tested every 3-12 weeks, preferably every 6 weeks.

Embodiment 6 relates to a method of stabilizing IBD using any one of the methods of embodiments 1 to 5.

Embodiment 7 relates to a method of augmenting pharmaceutical therapy by using any one of the methods of embodiments 1 to 6.

Embodiment 8 relates to the method of embodiment 2, wherein neutrophils are measured comprising the steps of measuring the neutrophils at baseline at the time of initial treatment, and monitored for reduction in neutrophils at regular intervals, and increasing the dosage at a rate of 20% per interval until neutrophils reach an acceptable level.

Embodiment 9 relates to the method of embodiment 2, wherein lymphocytes are measured comprising the steps of measuring the lymphocytes at baseline at the time of initial treatment, and monitored for increase in lymphocytes at regular intervals, and increasing the dosage at a rate of 20% per interval until lymphocytes reach an acceptable level.

Embodiment 10 relates to the method of embodiment 2, wherein lymphocytes are measured comprising the steps of measuring both neutrophils and lymphocytes at baseline, at the time of initial treatment, and monitoring both neutrophils and lymphocytes at regular intervals and based upon the neutrophils/lymphocyte ratio, and increasing the dosage at a rate of 20% per interval until such ratio reaches an acceptable level.

Embodiment 11 relates to the method of embodiment 2, wherein mean red cell distribution of width is measured comprising the steps of measuring both mean red cell distribution of width at baseline, at the time of initial treatment, and monitoring mean red cell distribution of width at regular intervals and based upon the mean red cell distribution of width, and increasing the dosage at a rate of 20% per interval until such distribution reaches an acceptable level.

Embodiment 12 relates to the method of any one of embodiments 8 to 11, wherein the method uses more that one of each of the methods of Neutrophil levels, Lymphocyte levels, the neutrophil/lymphocyte ratio, and the mean red cell distribution of width to direct therapy.

Embodiment 13 relates to a method of augmenting pharmaceutical therapy by using any one of the methods of embodiments 8 to 12.

Embodiment 14 relates to a method of treatment of IBD comprising administering the formulation of Formula X, wherein the formulation further comprising at least one additive comprising: (i) an amino acid; (ii) a peptide; (iii) a protein; (iv) a lipid; (v) a vitamin; (vi) a carbohydrate; (vii) a nucleic acid; (viii) a mineral; (ix) an anabolic nutrient; (x) an antioxidant; (xi) a probiotic bacterial strain; (xii) a lipotropic agent; (xiii) a flavoring agent; (xiv) a dye; (xv) a flow modifier; (xvi) a preservative; (xvii) a filler; (xviii) a binder; (xix) a dispersing agent; (xx) a human milk oligosaccharide, or (xxi) IMO, (xxii) an FDA approved fiber, or any combination thereof.

Embodiment 15 relates to a method of treatment of IBD comprising administering the formulation essentially comprising Curcumin, fenugreek, Xanthohumol, Folate, Vitamin B12, Ginger, Rosemary, Quercetin, protein, essential amino acids and branch-chain amino acids, alpha-linolenic acid.

Embodiment 16 relates to the method of any one of embodiments 1 to15, wherein the formulation essentially comprising Curcumin formulated with fenugreek, Xanthohumol from spent hops in a protein matrix, Folate, Vitamin B12, Ginger, Rosemary, and Quercetin.

Embodiment 17 relates to a method of treatment of IBD comprising administering the formulation of any one of embodiments 1 to 16 from about 0.3 g/kg/day to about 2.2 g/kg/day.

Embodiment 18 relates to a method of determining the proper dosage of a formulation of Formula X using the methods of any one of embodiments 1 to 17.

Embodiment 19 relates to a method of adjusting pharmaceutical treatment in conjunction with the formulation of Formula X comprising the methods of any one of embodiments 1 to 18.

Embodiment 20 relates to a method of confirming IBD in a patient, comprising the method of embodiment 2.

Embodiment 21 relates to a method of monitoring treatment of IBD using the formulation of Formula X using a blood test comprising the parameters of the method of embodiment 2.

Embodiment 22 relates to a method of returning Neutrophil levels, Lymphocyte levels, the neutrophil/lymphocyte ratio, or the mean red cell distribution width to normal using the formulation of embodiment 1.

Embodiment 23 relates to a method for treating ulcerative colitis or Crohn's disease in a subject in need thereof comprising administering to said subject an effective amount of Formula X, using the method of any one of embodiments 1 to 22 to determine the effective amount.

Embodiment 24 relates to a method for treating Crohn's disease in a subject in need thereof using the method of any one of embodiments 1 to 23.

Embodiment 25 relates to a method for treating ulcerative colitis in a subject in need thereof using the method of any one of embodiments 1 to 23.

Embodiment 26 relates to the method according to embodiment 2 for assessing whether a subject showing no symptoms or few symptoms of IBD is suffering from Crohn's disease or Ulcerative colitis in remission.

Embodiment 27 relates to the method of embodiment 1, wherein the dosage for the Formula X is adjusted by taking into account the parameters measured herein, wherein the parameter's measures are Neutrophil levels, Lymphocyte levels, the neutrophil/lymphocyte ratio, and the mean red cell distribution width, and wherein the dosage of the formulation of Formula X is two scoops of the product twice per day.

Embodiment 28 relates to the method of embodiment 1, wherein the dosage begins as a partial dosage of one half scoop of the formulation once per day, that is then increased incrementally based on patient tolerance wherein, if the patient tolerates the starting dosage of one half scoop once in a day, the dosage is increased to half a scoop twice per day, and if tolerated, it is increased to one full scoop twice per day, and if tolerated then to two full scoops twice per day.

Embodiment 29 relates to a method of support of symptoms of IBD comprising administering the formulation Formula X, according to embodiment 1.

Embodiment 30 relates to a method of support of symptoms of IBD comprising administering the formulation comprising curcumin, (curcuminoids from turmeric root/ Curcuma longa and galactomannans from fenugreek/Trigonella foenum-graecum seed fiber having about 40% curcuminoids), hops/Humulus lupulus extract (having about at least 2.5% xanthohumol), ginger root/Zingiber officinale extract, rosemary leaf/Rosmarinus officinalis extract, folate, vitamin B12 and optionally quercetin.

Embodiment 31 relates to a method of support of symptoms of IBD comprising administering the formulation comprising curcumin, (curcuminoids from turmeric root/ Curcuma longa and galactomannans from fenugreek/Trigonella foenum-graecum seed fiber having about 40% curcuminoids), hops/Humulus lupulus extract (having about at least 2.5% xanthohumol, preferably in a protein matrix), ginger root/Zingiber officinale extract, rosemary leaf/Rosmarinus officinalis extract, folate, vitamin B12 according to embodiment 30.

Embodiment 32 relates to a method of treatment of IBD comprising administering the formulation comprising curcumin, galactomannans from fenugreek/Trigonella foenum-graecum seed fiber, hops/Humulus lupulus extract (having about at least 2.5% xanthohumol, preferably in a protein matrix), ginger root/Zingiber officinale extract, rosemary leaf/Rosmarinus officinalis extract, folate, vitamin B12 and optionally quercetin, defined as Formula X.

Embodiment 32 relates to a use of curcumin, galactomannans from fenugreek/Trigonella foenum-graecum seed fiber, hops/Humulus lupulus extract (having about at least 2.5% xanthohumol, preferably in a protein matrix), ginger root/ Zingiber officinale extract, rosemary leaf/Rosmarinus officinalis extract, folate, vitamin B12 and optionally quercetin in the manufacture of a medicament for the treatment of IBD.

Each aspect so defined may be combined with any other aspect or aspects of the embodiments of the invention. In particular, any feature indicated as being optional or advantageous may be combined with any other feature or features indicated as being optional or advantageous.

In an effort to further illustrate the embodiments herein, this disclosure includes the following non-limiting examples:

Examples

Exemplary Composition

An exemplary composition including a curcumagalactomannoside and a hops extract is formulated as shown in Table 2 below. Nutritional information for the exemplary composition is shown in Table 3 below. The exemplary composition was manufactured and supplied by Metagenics, Inc. (Aliso Viejo, Calif., USA) and contained several phytonutrients and botanical extracts. Micronutrients were also included in keeping with clinical practice.

TABLE 2

Formulation of the exemplary composition

| Component | Amount |
| --- | --- |
| Curcumagalactomannoside | 250 mg |
| Hops extract | 250 mg |
| Ginger root extract | 200 mg |
| Quercetin | 100 mg |
| Rosemary extract | 100 mg |
| Folate | 200 mcg |
| Vitamin B12 | 3 mcg |
| Protein | 13 g |

The curcumagalactomannoside was a mixture of curcuminoids from turmeric root/Curcuma longa and galactomannans from fenugreek/Trigonella foenum-graecum seed fiber, standardized to 40% curcuminoids, and is commercially available.

The hops extract/Humulus lupulus extract was standardized to 2.5% xanthohumol coupled to a rice protein matrix, and is commercially available.

The ginger root extract/Zingiber officinale extract was standardized to 5% pungent compounds, and is commercially available.

Rosemary extract/Rosmarinus officinalis extract, and is commercially available

Folate is commercially available.

Vitamin B-12 is commercially available.

Quercetin is commercially available.

Protein includes 16 g of total protein with added amino acids: L-lysine, L-leucine, L-glutamine, L-valine, and L-isoleucine, and is commercially available.

TABLE 3

Nutritional information of the exemplary composition

| | Amount Per Serving |
| --- | --- |
| Serving Size | 47 g |
| Calories | 170 |
| Total Fat | 7 g |
| Cholesterol | 0 mg |
| Sodium | 120 mg |
| Potassium | 350 mg |
| Total Carbohydrate | 16 g |
| Dietary Fiber | 6 g |
| Sugars | 4 g |

Exemplary Composition Evaluation

Ten adults age 18-70 years with previously-diagnosed ulcerative colitis or Crohn's disease were recruited. Exclusion criteria were as follows: currently taking the study formulation or similar products/formulations (macronutrient and micronutrient support consumed as a beverage); currently taking turmeric, curcumin, fenugreek, hops, xanthohumol, ginger, rosemary or quercetin supplements; currently receiving intravenous nutrient support; currently taking anti-coagulant or anti-platelet medications; currently taking oral or intravenous antibiotic, antiparasitic, or antifungal medications; initiation of or changes to medications, supplements, an exercise regime, or a nutrition plan within twenty-eight days prior to screening; currently participating in a weight loss program; gastrointestinal surgery within three months prior to screening; currently have a colostomy or ileostomy bag in place; malignancy within the last five years; women who were lactating, pregnant or planning pregnancy during the study period; known intolerance or allergy to ingredients in the study product; or participating in another interventional research study or within twenty-eight days prior to screening. The study protocol was registered at ClincalTrials.gov.

Demographic parameters of the ten participants enrolled in the study are described in the table below. To meet the recruitment target, thirty-three individuals were assessed for eligibility; twenty-three were excluded and ten individuals were enrolled in the study and began taking the study product. One participant dropped out three weeks before completing the protocol, citing non-serious adverse events (worsening of pre-existing gastrointestinal symptoms). Data from nine participants that completed the study were analyzed. Overall study adherence was excellent.

TABLE 4

Participant Demographics at Baseline (n = 10)

| | Mean +/− SD or n (%) |
|---|---|
| Age (years) | 39.3 +/− 13.5 |
| Body mass index (kg/m$^2$) | 28.3 +/− 3.4 |
| Gender | |
| Males | 2 (20%) |
| Females | 8 (80%) |
| Condition | |
| Ulcerative colitis | 5 (50%) |
| Crohn's disease | 5 (50%) |
| Years since initial IBD diagnosis | 11.2 +/− 6.3 |
| Race, ethnicity | |
| White, not Hispanic or Latino | 10 (100%) |
| Tobacco | |
| User | 2 (20%) |
| Non-user | 8 (80%) |
| Alcohol use (# alcoholic beverages/week) | 2.6 +/− 4.4 |
| IBD Prescription Medications | |
| Salicylates (oral mesalamine) | 4 (40%) |
| Purine antagonists (azathioprine, mercaptopurine) | 2 (20%) |
| TNF blockers (adalimumab) | 1 (10%) |
| Glucocorticoids (budesonide) | 1 (10%) |

The study was a single-arm, open-label, pre-post study to assess the effect of the nutrition support formula on blood nutrient levels in adults with ulcerative colitis or Crohn's disease over a twelve-week period. Adherence, safety and tolerability of the product were also monitored throughout the study. Participants were screened for eligibility over the phone, then screened in person. Qualifying participants returned for a baseline visit, a mid-study visit after six weeks, and a study end visit after 12 weeks.

Participants were asked to add two scoops of the exemplary composition (44 grams) to water or juice (8-10 ounces) and consume it twice per day as a reconstituted beverage.

Fasting blood samples were obtained at the baseline visit and after 12 weeks of treatment. A complete blood count and comprehensive metabolic panel indicated no adverse changes; all mean values were within normal laboratory reference ranges at baseline and at the end of the study. However three blood count parameters were altered significantly as described below:

Red cell distribution width (RDW): RDW decreased 9.2% (p=0.012). RDW is an indicator of red blood cell volume heterogeneity (anisocytosis). RDW cutoff (the point where the results are normal vs. abnormal indicating disease) for ulcerative colitis is 14.0, and for Crohn's Disease 14.1. Patients in the examples had RDW of greater than 14.1 at baseline, and less than 14.0 after 12 weeks of treatment. The results suggest that RDW is an emerging marker of IBD disease activity. RDW represents a surrogate marker of disease activity, even in the absence of symptoms in patients with IBD. In the current investigation, mean RDW decreased from 14.8% to 13.4%-14% is the cutoff for "normal" results (within the laboratory reference range). The reduction in RDW below previously defined cut-offs for distinguishing active disease from inactive disease appear to indicate a modulation of disease activity.

Neutrophil to lymphocyte ratio (NLR): Percent neutrophils decreased 10.4% (p=0.042), and absolute lymphocyte count increased 18.6% (p=0.048). NLR was calculated by dividing absolute neutrophil count by absolute lymphocyte count. Mean NLR decreased from 2.61 at baseline to 2.13 after the twelve-week intervention (NS, p=0.061). The NLR cutoff for active disease is 2.47. The mean NLR value was greater than 2.47 at baseline and moved below the cutoff after 12 weeks treatment. NLR appears to be a predictive marker of disease activity in patients with ulcerative colitis and Crohn's disease. Additionally the decrease in neutrophil count (from 64.3 to 57.6 after 12 weeks of treatment) and increase in lymphocyte percentage (from 26.4 at baseline to 32.1 at 12 weeks of treatment), along with minimal change in total leukocyte count, indicated a modulatory effect on leukocyte subtype. The twelve-week course of treatment provided decreases in neutrophils, which have been identified as a potential target for managing inflammation in patients with IBD.

Validated questionnaires to monitor quality of life and symptoms are tabulated in Table 5. The Gastrointestinal Quality of Life Index (GIQLI) and the Inflammatory Bowel Disease Questionnaire (IBDQ) were administered at the baseline, mid-study, and study end visits. There was a high correlation between symptoms and RDW and NLR.

TABLE 5

Quality of Life Questionnaires

| Score | Baseline | | Mid-Study | | 12 Weeks | | % Δ mean | |
|---|---|---|---|---|---|---|---|---|
| | Range | Mean | SE | Mean | SE | Mean | SE | 12 Wks | p-val |
| GIQLI - Total | 0-144 | 94.1 | 5.6 | 90.2 | 5.6 | 101.3 | 5.7 | 7.7% | 0.079 |
| GIQLI - Gastrointestinal Symptoms | 0-76 | 54.0 | 2.9 | 50.3 | 2.9 | 57.0 | 2.9 | 5.6% | 0.070 |

TABLE 5-continued

Quality of Life Questionnaires

| | Score Range | Baseline Mean | Baseline SE | Mid-Study Mean | Mid-Study SE | 12 Weeks Mean | 12 Weeks SE | % Δ mean 12 Wks | p-val |
|---|---|---|---|---|---|---|---|---|---|
| GIQLI - Physical Function | 0-28 | 13.9 | 1.7 | 13.0 | 1.7 | 14.8 | 1.8 | 6.5% | 0.358 |
| GIQLI - Social Function | 0-16 | 10.6 | 0.9 | 10.8 | 0.9 | 12.4 | 0.9 | 17.3% | 0.092 |
| GIQLI - Emotional Function | 0-20 | 12.9 | 1.0 | 13.3 | 1.0 | 14.2 | 1.0 | 9.9% | 0.279 |
| GIQLI - Subjective Treatment Assessment | 0-4 | 2.7 | 0.3 | 2.8 | 0.3 | 3.0 | 0.3 | 11.4% | 0.549 |
| IBDQ - Total | 32-224 | 161.4 | 8.9 | 157.8 | 8.9 | 165.6 | 9.2 | 2.6% | 0.592 |
| IBDQ - Bowel Symptoms | 10-70 | 51.1 | 2.6 | 48.6 | 2.6 | 54.1 | 2.7 | 5.9% | 0.291 |
| IBDQ - Systemic Systems | 5-35 | 20.5 | 1.6 | 19.5 | 1.6 | 21.0 | 1.6 | 2.3% | 0.535 |
| IBDQ - Social Function | 5-35 | 29.0 | 2.0 | 28.2 | 2.0 | 29.8 | 2.0 | 2.7% | 0.653 |
| IBDQ - Emotion Health | 12-84 | 60.8 | 4.1 | 61.5 | 4.1 | 60.9 | 4.2 | 0.2% | 0.950 |

Continuous measures are presented as mean and standard error at each time point. Changes in quality of life measures (GIQLI and IBDQ scores) were analyzed using a random intercept model with visit (baseline, six weeks, and twelve weeks) as a repeated factor. Statistical analyses were performed using SPSS v.20 software (IBM Corp., Armonk, N.Y.).

The examples shown above are not exhaustive, but are intended to provide guidance sufficient to practice the embodiments herein.

With regard to the description herein, where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit and an upper limit, is disclosed, any number falling within the range is specifically disclosed. In particular, the following numbers within the range are specifically disclosed: for example, when a variable ranges from 1 percent to 100 percent, this disclosure explicitly includes 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any ratio, expressed as a range defined by two numbers as each number, and variations between listed whole numbers is also specifically disclosed. Use of the term "optionally" with respect to any element of the embodiment, whether included in a claim or not means that the element is required, or alternatively, the element is not required, both alternatives being within the scope of the invention. Use of broader terms such as comprises, includes, and having should be understood to provide support for narrower terms such as consisting of, consisting essentially of, and comprised substantially of.

Additionally, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Likewise, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

Lastly, it is to be understood that the appended claims are not limited to express and particular compounds, compositions, or methods described in the detailed description, which may vary between particular embodiments which fall within the scope of the appended claims. As such, with respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of embodiments and independent and dependent claims, including those related to or dependent on single and/or multiple embodiments and claims, are herein expressly contemplated.

The invention claimed is:

1. A composition for treatment of inflammation in a mammal, the mammal having a neutrophil to lymphocyte ratio (NLR), the composition comprising:
 a curcumagalactomannoside; and
 a hops extract;
 wherein the curcumagalactomannoside and the hops extract cooperate to decrease the NLR of the mammal 12 weeks after ingestion of the composition.

2. The composition of claim 1, wherein the curcumagalactomannoside is derived from a curcuminoid and a galactomannan.

3. The composition of claim 2, wherein the curcuminoid is present in the curcumagalactomannoside in an amount of from about 20 wt. % to about 60 wt. % based on a total weight of the curcumagalactomannoside.

4. The composition of claim 1, wherein the curcumagalactomannoside is present in the composition in an amount of from about 0.01 wt. % to about 10 wt. % based on a total weight of the composition.

5. The composition of claim 1, wherein the hops extract comprises xanthohumol.

6. The composition of claim 1, comprising a protein-containing matrix, the protein-containing matrix comprising the hops extract.

7. The composition of claim 6, wherein the hops extract is present in the protein-containing matrix in an amount of from about 1 wt. % to about 95 wt. % based on a total weight of the protein-containing matrix.

8. The composition of claim 1, wherein the hops extract is present in the composition in an amount of from about 0.01 wt. % to about 10 wt. % based on a total weight of the composition.

9. The composition of claim 1, further comprising a ginger root extract.

10. The composition of claim 9, wherein the ginger root extract comprises a pungent compound in an amount of from about 0.1 wt. % to about 20 wt. % based on a total weight of the ginger root extract.

11. The composition of claim 1, further comprising aquercetin, rosemary extract, folate, vitamin B-12, or combinations thereof.

12. The composition of claim 1, further comprising an amino acid, a peptide, a protein, a lipid, a vitamin, a carbohydrate, a nucleic acid, a mineral, an anabolic nutrient, an antioxidant, a probiotic bacterial strain, a lipotropic agent, a flavoring agent, a dye, a flow modifier, a preservative, a filler, a binder, a dispersing agent, a human milk oligosaccharide, isomalto-oligosaccharide, a fiber, or combinations thereof.

13. The composition of claim 12, wherein the amino acid is present and the amino acid is selected from the group consisting of L-lysine, L-leucine, L-glutamine, L-valine, L-isoleucine, and combinations thereof.

14. A composition for treatment of inflammation in a mammal, the mammal having a neutrophil to lymphocyte ratio (NLR), the composition consisting essentially of:
 curcumagalactomannoside;
 a hops extract;
 a ginger root extract;
 a protein-containing matrix;
 a rosemary leaf extract;
 folate;
 vitamin B-12; and
 quercetin;
 wherein at least the curcumagalactomannoside and hops extract cooperate to decrease the NLR of the mammal 12 weeks after ingestion of the composition.

15. A composition for treatment of inflammation in a mammal, the mammal having a neutrophil to lymphocyte ratio (NLR), the composition comprising:
 a curcumagalactomannoside; and
 a protein-containing matrix;
 wherein the protein-containing matrix comprises a hops extract; and
 wherein the curcumagalactomannoside and the hops extract cooperate to decrease the NLR of the mammal 12 weeks after ingestion of the composition;
 optionally, wherein the hops extract is present in the protein-containing matrix in an amount of from about 1 wt. % to about 95 wt. % based on a total weight of the protein-containing matrix.

16. The composition of claim 15, wherein the curcumagalactomannoside is derived from a curcuminoid and a galactomannan, optionally wherein the curcuminoid is present in the curcumagalactomannoside in an amount of from about 20 wt. % to about 60 wt. % based on a total weight of the curcumagalactomannoside.

17. The composition according to claim 15, wherein the hops extract is present in the protein-containing matrix in an amount of from about 1 wt. % to about 95 wt. % based on a total weight of the protein-containing matrix.

18. The composition of claim 17, wherein:
 i) the curcumagalactomannoside is present in the composition in an amount of from about 0.01 wt. % to about 10 wt. % based on a total weight of the composition; and
 ii) the hops extract is present in the composition in an amount of from about 0.01 wt. % to about 10 wt. % based on a total weight of the composition.

* * * * *